United States Patent
Nashner

(10) Patent No.: US 7,500,752 B2
(45) Date of Patent: Mar. 10, 2009

(54) DIAGNOSING AND TRAINING THE GAZE STABILIZATION SYSTEM

(75) Inventor: Lewis M. Nashner, Portland, OR (US)

(73) Assignee: Natus Medical Incorporated, San Carlos, CA (US)

(*) Notice: Subject to any disclaimer, the term of this patent is extended or adjusted under 35 U.S.C. 154(b) by 0 days.

(21) Appl. No.: 11/673,686

(22) Filed: Feb. 12, 2007

(65) Prior Publication Data

US 2007/0121066 A1    May 31, 2007

Related U.S. Application Data

(63) Continuation-in-part of application No. 11/117,714, filed on Apr. 28, 2005, now Pat. No. 7,195,355.

(60) Provisional application No. 60/565,905, filed on Apr. 28, 2004.

(51) Int. Cl.
A61B 3/14    (2006.01)
A61B 3/02    (2006.01)

(52) U.S. Cl. .................... 351/210; 351/237

(58) Field of Classification Search ............ 351/200, 351/203, 209–211, 222–224, 237
See application file for complete search history.

(56) References Cited

U.S. PATENT DOCUMENTS

| | | |
|---|---|---|
| 4,034,401 A | 7/1977 | Mann |
| 4,738,269 A | 4/1988 | Nashner |
| 4,807,986 A | 2/1989 | Wasserman |
| 4,830,024 A | 5/1989 | Nashner |
| 4,838,681 A | 6/1989 | Pavlidis |
| 5,052,406 A | 10/1991 | Nashner |
| 5,180,907 A | 1/1993 | Udden et al. |
| 5,303,715 A | 4/1994 | Nashner et al. |
| 5,474,087 A | 12/1995 | Nashner |
| 5,478,239 A | 12/1995 | Fuerst et al. |
| 5,697,791 A | 12/1997 | Nashner et al. |
| 5,942,954 A | 8/1999 | Galiana et al. |
| 5,953,102 A * | 9/1999 | Berry .................... 351/247 |
| 6,106,119 A | 8/2000 | Edwards |
| 6,796,947 B2 | 9/2004 | Watt et al. |
| 6,997,556 B2 | 2/2006 | Pfleger |
| 2002/0011250 A1 | 1/2002 | Stewart et al. |
| 2002/0151818 A1 | 10/2002 | Watt et al. |

(Continued)

OTHER PUBLICATIONS

Baloh et al "Disorders of the Vestibular System" edited by Robert W. Baloh and G. Michael Halmagyi, Chapters 3 and 6, Oxford University Press, New York, 1996.

(Continued)

*Primary Examiner*—Scott J Sugarman
*Assistant Examiner*—Dawayne A Pinkney
(74) *Attorney, Agent, or Firm*—Temmerman Law Office; Mathew J. Temmerman

(57) ABSTRACT

A method for diagnosing impairments of a subject's gaze stabilization system is provided. The method includes measuring the subject's static visual acuity to obtain an assessment, setting at least one test parameter based on the assessment, measuring the subject's dynamic visual acuity using the test parameters to obtain a first dynamic measurement and a second dynamic measurement, and determining an impairment of the subject's gaze stabilization system using the assessment and the first and second dynamic measurements.

24 Claims, 10 Drawing Sheets

U.S. PATENT DOCUMENTS

2003/0086061 A1    5/2003    Pfleger
2004/0075814 A1*   4/2004    Alster et al. ................ 351/246
2004/0162169 A1*   8/2004    Gallagher ................... 473/564

OTHER PUBLICATIONS

Nashner et al. "Head-trunk movement coordination in the standing posture," Chapter 21, Vestibulospinal Control of Posture and Locomotion, Progress in Brain Research, vol. 76, Amsderdam Elsevier Science Publishers, pp. 243-251, 1988.

Shepard et al. "Rotational Chair Testing" in Practical Management of the Balance Disorder Patient, Chapter 6, Singular Publishing Group, Inc., San Diego, pp. 221,1996.

Shepard et al., "Electronystagmography Ealuation" in Practical Management of the Balance Disorder Patient, Chapter 4, Singular Publishing Group, Inc., San Diego, pp. 221, 1996.

Demer et al. "Dynamic visual acuity: a test for oscillopsia and vestibule-ocular reflex function," American Journal of Otology, vol. 15, pp. 340-347, 1994.

Herdman et al. "Computerized dynamic visual acuity test in the assessment of vestibular deficits," American Journal of Otology vol. 19, pp. 790-796, 1998.

Koles et al. "The relationship between body sway and foot pressure in normal man," Journal of Medical Engineering and Technology, vol. 4, pp. 279-285, 1980.

* cited by examiner

Preliminary Form

Test Forms

Preliminary Form

Test Forms

Preliminary Form

Test Forms

Preliminary Form

Test Forms

DIAGNOSING AND TRAINING THE GAZE STABILIZATION SYSTEM

CROSS-REFERENCE TO RELATED APPLICATIONS

This patent application is a continuation-in-part of U.S. patent application Ser. No. 11/117,714 filed Apr. 28, 2005, which claims priority under U.S.C. § 119(e) to U.S. Provisional Patent Application No. 60/565,905 filed Apr. 28, 2004, the disclosures of which are incorporated by reference herein in their entirety.

FIELD OF THE INVENTION

The invention generally relates to gaze stabilization and, more particularly, the invention relates to isolating and quantifying impairments of the gaze stabilization system.

BACKGROUND OF THE INVENTION

In subjects with chronic balance disorders, approaches to medical treatment based on drugs and surgery can be effective in stabilizing the pathological processes that cause the disorders. In such subjects, these approaches can sometimes stabilize but seldom fully resolve the underlying pathological manifestations of the balance problem. Once the underlying pathological processes are medically stable, however, rehabilitation exercises frequently prove effective in reducing many of the disabling symptoms and functional problems associated with chronic balance disorders. Hence, effective treatment of chronic balance disorders typically employs combinations of medical and rehabilitation exercise treatments.

In selecting medical treatments most likely to stabilize underlying pathological processes, clinicians first determine the location, nature, and extent of the underlying pathological process. To make pathological determinations, clinicians typically rely on the results of the subject history and physical examination to develop diagnostic hypotheses, and then use site-of-lesion laboratory tests to confirm or rule out their hypotheses. In designing effective rehabilitation exercise programs, in contrast, clinicians require additional knowledge of the subject's functional impairments and adaptive response capabilities. For this reason, objective tests that isolate and quantify the functional impairments associated with balance disorders complement the information provided by site-of-lesion tests and complete the clinical information necessary for effective treatment planning and outcome documentation.

To develop methods and devices for isolating and quantifying functional impairments of the balance system, it is first necessary to understand the functional organization of the balance system. The balance system includes a number of processes that may be grouped into distinct but interdependent systems—one responsible for gaze stabilization and the other responsible for postural stabilization. The gaze stabilization system maintains the gaze direction of the eyes relative to surrounding visual targets as the subject or targets moves within the subject's environment. Information useful in managing patients with chronic balance disorders may be provided by assessing their ability to maintain dynamic visual acuity. Dynamic visual acuity refers to a subject's ability to accurately perceive a visual object while either the subject moves and the visual object is fixed, the visual object moves and the subject is fixed, or the subject and the visual object are moving independently. When the subject and/or the visual object are moving, subjects whose gaze control system functions normally can maintain their visual acuity by continuously moving their eyes to stabilize their direction of gaze relative to the visual object. Stabilizing the direction of gaze while a person moves maintains their visual acuity during activities involving active head and body movements. When individuals with impaired gaze stabilization participate in activities involving self-motion and moving objects in the surrounds, moving objects may appear blurred while stationary objects may become blurry and sometimes appear to be in motion.

Individuals with normal visual function achieve their best visual acuity when the viewed visual object is focused on a position fixed on the fovea, a small region located at the approximate center of the retina of the eye. The fovea contains the highest density or concentration of visual or cone receptors. Acuity is substantially reduced when the position of an object is displaced more than a few degrees of visual angle from the center of the fovea, and/or when the object is moving faster than two degrees per second. However, the time it takes the brain to perceive an object is short, and these precise position and velocity requirements need to be maintained for no longer than approximately 25 milliseconds for accurate perception to occur. In subjects with a history of brain disorders, two examples being stroke and traumatic brain injury, the minimum time for accurate perception to occur may be substantially increased to 100 milliseconds or more.

A detailed discussion of gaze stabilization may be found in "Disorders of the Vestibular System" edited by Robert W. Baloh and G. Michael Halmagyi and published by Oxford University Press, New York, in 1996 (Chapter 3 *How Does the Vestibulo-ocular Reflex Work?*, and Chapter 6, *How Does the Visual System Interact with the Vestibulo-ocular Reflex?*), both chapters of which are hereby incorporated herein by reference. In summary, gaze is stabilized on visual objects under a wide variety of subject and object movement combinations encountered in daily life through the cooperative interactions of five movement control systems: (1) the vestibulo-ocular reflex (VOR) system; (2) the smooth pursuit eye movement system; (3) the saccadic movement system; (4) the optokinetic movement system; and (5) the vergence eye movement system. Because the gaze stabilization system is highly adaptive, which one or combination of control systems is used varies depending on the specific conditions of the subject and visual object motion.

A number of research studies have examined the dynamic visual acuity of subjects exposed to visual objects while the subject and/or the visual target were moving. These studies were primarily concentrated on the ability of the VOR system to stabilize a subject's gaze when the subject moves and the visual object is fixed. For example, a series of studies by Demer and colleagues quantified the ability of subjects to accurately perceive fixed visual targets in the presence of active and passive head rotations. However, because isolating and quantifying the functional performance of the individual eye movement control systems were not goals in these studies, they did not disclose methods for displaying and moving visual objects that can achieve reliable isolation of the performance of individual eye movement control systems.

Aznar-Casanova et al. (2005) examined the effects of moving a relatively large visual area at different fixed velocities on the minimum spatial frequencies that could be perceived by their subjects. However, their subjects were exposed to predictably moving visual fields for periods as long as 14 seconds. Because predictable visual object motions were used, their methods could not be used to reliably isolate (predictive) saccadic eye movements from the smooth pursuit and optokinetic movements. Haarmeier and Thieer (1999) examined the visual acuity of normal subjects and patients viewing visual objects smoothly moving over a range of velocities. However, the direction of object movements was always to the right and the acuity test always administered 250 milliseconds following the onset of movement. Because several features of visual object motions were predictable, subjects may have been able to substitute predictive saccadic movements.

SUMMARY OF THE INVENTION

In accordance with one aspect of the invention, a method for diagnosing impairments of a subject's gaze stabilization system includes measuring the subject's static visual acuity to obtain an assessment, measuring the subject's minimum perception time to obtain a perception time assessment, setting test parameters based on the static visual acuity and minimum perception time assessments, measuring the subject's dynamic visual acuity using the test parameters to obtain a first dynamic measurement and a second dynamic measurement, and determining an impairment of the subject's gaze stabilization system using the assessment and the first and second dynamic measurements.

In accordance with related embodiments, the subject's dynamic visual acuity may be measured when a subject's head is fixed and the display object is continuously moving, when the subject's head is fixed and the display object is discontinuously moving, when the subject's head is fixed and the display object is continuously moving and is displayed in a patterned large field background, when the subject's head is moving and the display object is fixed, when a subject's head is moving and a display object is continuously moving, when a subject's head is moving and a display object is discontinuously moving, and/or when the subject's head is moving and the display object is continuously moving and is displayed in a patterned large field background. Measuring the subject's dynamic visual acuity may include displaying a preliminary form and displaying a test form of the display object. The assessment may include a minimum interval for the subject to correctly identify a visual object, the minimum interval may be based on the minimum perception time, the test parameters may include a display interval that is greater than or equal to the minimum interval, and the test form may be displayed for the display interval.

In accordance with other related embodiments, measuring the subject's visual acuity when the subject's head is fixed and the display object is continuously moving and is displayed in a patterned large field background may include when the patterned large field background is moving in relation to the moving display object and/or when the patterned large field background is fixed in relation to the moving display object. The method may further include determining a first maximum velocity of a visual object that the subject correctly perceives using the subject's smooth pursuit system, wherein measuring the subject's dynamic visual acuity may include displaying the display object moving at a velocity less than the first maximum velocity. The assessment may include a minimum size of a visual object that the subject correctly identifies, the test parameters may include a display size that is greater than or equal to the minimum size, and the display object may be displayed at the display size.

In accordance with other related embodiments, measuring the subject's visual acuity when the subject's head is fixed and the display object is continuously moving and is displayed in a patterned large field background may include when the patterned large field background is moving in relation to the moving display object and/or when the patterned large field background is fixed in relation to the moving display object. The method may further include determining a second maximum velocity of a visual object that the subject correctly perceives using the subject's optokinetic system. Measuring the subject's dynamic visual acuity may include displaying the display object imbedded within a large field background and moving the object and the background together at a velocity equal to or greater than the first maximum velocity. The assessment may include a minimum size of a visual object that the subject correctly identifies, the test parameters may include a display size that is greater than or equal to the minimum size, and the display object may be displayed at the display size.

In accordance with other related embodiments, measuring the subject's visual acuity when the subject's head is fixed and the display object is discontinuously moving may include instructing the subject to direct gaze towards a focus point (such as a center marker), causing the display object to abruptly appear after a random delay at a predetermined location relative to the center marker, presenting the display object for a predetermined period of time, instructing the subject to identify the object, and then determining a minimum presentation time required by the subject to correctly identify the display object at a second location over a plurality of trials. For example, the display object size may be twice the size of the smallest object correctly identified during the static visual acuity test. Additional minimum presentation times may be calculated for display objects placed in various directions from the central marker (e.g., to the right, left, above, and below). The method may further include measuring the subject's dynamic visual acuity to obtain a third dynamic measurement, wherein determining an impairment of the subject's gaze stabilization system may include using the assessment and the first, second and third dynamic measurements. The method may further include measuring the subject's dynamic visual acuity to obtain a fourth dynamic measurement, wherein determining an impairment of the subject's gaze stabilization system may include using the assessment and the first, second, third and fourth dynamic measurements. The method may further include measuring the subject's dynamic visual acuity to obtain a fifth dynamic measurement, wherein determining an impairment of the subject's gaze stabilization system may include using the assessment and the first, second, third, fourth and fifth dynamic measurements.

In accordance with other related embodiments, the method may further include having the subject perform at least one free standing balance task while measuring the subject's dynamic visual acuity. Having the subject perform at least one free standing balance task may include having the subject stand on at least one surface which moves in relation to a display of the display object. The surface may be a force plate and/or a treadmill. Having the subject perform at least one free standing balance task may include surrounding the subject with a visual surround. Measuring the subject's dynamic visual acuity may include the subject's dynamic visual acuity related to the subject's vestibule-ocular reflex system, the subject's smooth pursuit eye movement system, the subject's optokinetic eye movement system and/or the subject's saccadic movement system.

In accordance with another aspect of the invention, a method for diagnosing impairments of a subject's gaze stabilization system includes measuring the subject's static visual acuity to obtain an assessment, measuring the subject's minimum perception time to obtain a second assessment, and measuring the subject's dynamic visual acuity to obtain a first dynamic measurement and a second dynamic measurement, wherein the subject's dynamic visual acuity is measured when a subject's head is fixed and a display object is continuously moving, when the subject's head is fixed and the display object is discontinuously moving, when the subject's head is moving and the display object is fixed and/or when the subject's head is fixed and the display object is continuously moving and is displayed in a patterned large field background, and wherein the display object is displayed in a preliminary form and a test form. The method further includes determining an impairment of the subject's gaze stabilization system using the assessment and the first and second dynamic measurements.

In accordance with related embodiments, the assessment may include a minimum interval for the subject to correctly identify a visual object, and the test form may be displayed for a display interval that is greater than or equal to the minimum interval. The minimum interval may be based on the second assessment of the minimum perception time. The assessment may include a minimum size of a visual object that the subject correctly identifies, and the display object may be displayed at a display size that is greater than or equal to the minimum size. The method may further include determining a first maximum velocity of a visual object that the subject correctly perceives using the subject's smooth pursuit system, wherein measuring the subject's dynamic visual acuity may include displaying the display object moving at a velocity equal to or less than the first maximum velocity. The method may further include determining a second maximum velocity of a visual object that the subject correctly perceives using the subject's optokinetic system. Measuring the subject's dynamic visual acuity may include displaying the display object imbedded within a large field background and moving the object and background at a velocity equal to or greater than the first maximum velocity.

In accordance with another aspect of the invention, a method for training a subject's gaze stabilization system includes measuring the subject's static visual acuity to obtain an assessment, displaying a display object to the subject, the display object having at least one parameter based on the assessment, having the subject maintain gaze on the display object when the subject is moving, when the display object is moving or both and while executing a gaze control task, determining a quantity related to proficiency of the subject's gaze performance at selected times during execution of the gaze control task, and displaying the one or more quantities to the subject.

In accordance with related embodiments, having the subject maintain gaze on the display object occurs when a subject's head is fixed and the display object is continuously moving, when the subject's head is fixed and the display object is discontinuously moving, when the subject's head is fixed and the display object is continuously moving and is displayed in a patterned large field background, when the subject's head is moving and the display object is fixed, when a subject's head is moving and a display object is continuously moving, when a subject's head is moving and a display object is discontinuously moving, and/or when the subject's head is moving and the display object is continuously moving and is displayed in a patterned large field background. The method may further include moving the display object according to a protocol and/or having the subject move according to a second protocol. Displaying a display object may include displaying a preliminary form and displaying a test form of the display object. The assessment may include a minimum interval for the subject to correctly identify a visual object and displaying the test form may include displaying the test form for a display interval that is greater than or equal to the minimum interval. The minimum interval may be based on the second assessment of the subject's minimum perception time.

In accordance with other related embodiments, the method may further include determining a first maximum velocity of a visual object that the subject correctly perceives using the subject's smooth pursuit system, wherein displaying a display object includes moving the display object at a velocity equal to or less than the first maximum velocity. The method may further include determining a second maximum velocity of a visual object that the subject correctly perceives using the subject's optokinetic system. Displaying a display object imbedded within a large field background may include moving the display object and the background at a velocity equal to or greater than the first maximum velocity. The assessment may include a minimum size of a visual object that the subject correctly identifies and displaying a display object may include displaying the display object at a display size that is greater than or equal to the minimum size. The method may further include having the subject perform at least one free standing balance task while executing the gaze control task. Having the subject perform at least one free standing balance task may include having the subject stand on at least one surface which moves in relation to a display of the display object. The surface may be a force plate and/or a treadmill. Having the subject perform at least one free standing balance task may include surrounding the subject with a visual surround. Determining a quantity related to proficiency of the subject's gaze performance may include the subject's gaze performance related to the subject's vestibule-ocular reflex system, the subject's smooth pursuit eye movement system, the subject's optokinetic eye movement system, the subject's saccadic movement system, the subject's vergence eye movement system, or any combination thereof.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Figure 1:
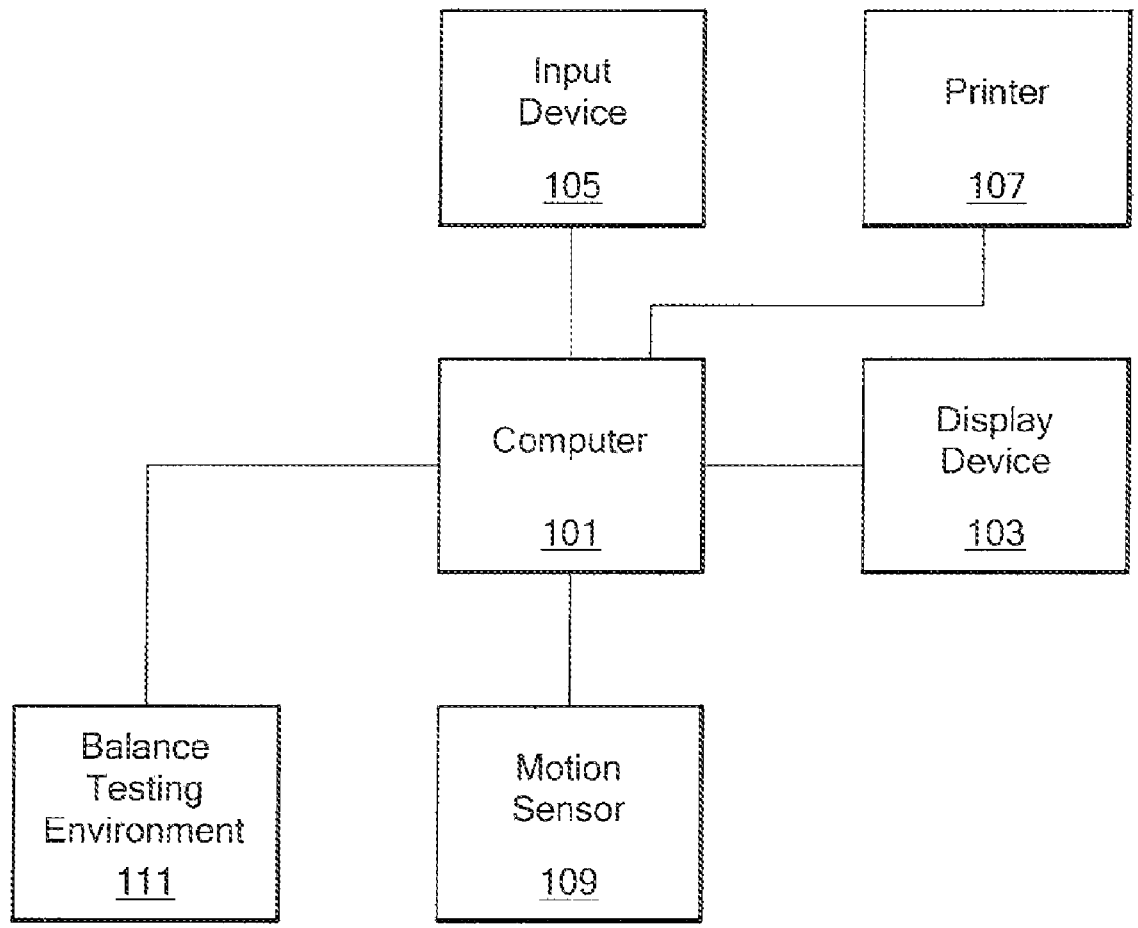
FIG. 1 is a block diagram illustrating a system which may be used to measure aspects of a subject's gaze stabilization system according to an embodiment of the present invention.

The visual system requires a minimum time to process and accurately perceive a visual image once it has been stabilized on the fovea. In healthy adult subjects this time varies between approximately 25-50 milliseconds. In elderly individuals or individuals with brain injuries affecting areas involved in visual processing, the minimum perception time may increase to 100 milliseconds or more.

The VOR system is a fast acting system that rotates the eyes in equal and opposite directions in relation to the rotations of the head. Movements can be initiated within 10 milliseconds of the onset of head movement, much earlier than either saccadic or smooth pursuit movements. However, because eye movements are driven by inputs from the semicircular canals of the vestibular system, they can stabilize a visual object on the fovea only when the head undergoes a rotational movement relative to a fixed visual object. Performance of this control system is further limited by the inability of the semicircular canals to measure rotational head motions at frequencies below approximately 0.1 Hz.

The smooth pursuit eye movement system enables individuals to continuously redirect their gaze such that a visual object moving continuously in relation to the subject (with the subject and/or the object moving) is maintained on the fovea. The accuracy of this system, however, is substantially reduced as movement velocities of the visual object relative to the subject increase beyond 20 to 30 degrees per second. In addition, the initiation of a smooth pursuit movement is delayed approximately 150 milliseconds or longer after a visual object first begins to move. Hence, on first presentation of a smoothly moving visual object, a subject must execute an "acquisition" saccadic movement to position the object on the fovea and only then can smoothly pursue the object. It is significantly slower than the VOR system, because the visual feedback information is mediated by complex pathways involving image processing within the visual cortex. In contrast to the VOR system, the smooth pursuit system is effective at the lowest frequencies of head movement and is equally accurate for movements in all directions.

The saccadic movement system generates rapid step-like eye movements that can accurately redirect gaze so that a visual object within the subject's wider field of view is rapidly repositioned onto the fovea. Saccadic movements to visual objects can be initiated in approximately 75 milliseconds and can move the eyes at velocities above 500 degrees per second, thereby stabilizing a displayed visual object on the fovea within approximately 200 milliseconds, depending on its initial distance from the fovea. The saccadic system also has the ability to anticipate the motions of visual objects that are moving predictably, and can launch a corrective movement without a time delay. However, because this system generates discrete step-like movements, it cannot continuously redirect gaze to maintain the direction of gaze relative to a continuously moving object.

The optokinetic movement system moves the eyes in the direction of continuous movements of large portions of the subject's visual field. Movement responses include two alternating phases, the pursuit phase during which the eyes move in conjunction with the large field motions of the surrounds and the saccadic phase during which the eyes rapidly move back to a central position. The optokinetic control system can accurately track large fields moving at velocities as high as 30 to 40 degrees per second. However, this system also requires time for the brain to perceive and process the information when first exposed to large field movements, and the initiation of the alternating smooth and saccadic movements is delayed several hundred milliseconds.

The vergence eye movement system causes the eyes to move in opposing directions. The vergence system is required to maintain an object centered on the foveae of both eyes when the distance between the object and the eyes changes. Because the two eyes are separated by a distance, the eyes must both move inward toward the nose as a visual object moves closer to the subject.

In addition to the above five eye movement control systems, there are reflexive, automatic and voluntary motor systems for moving the head relative to the body. These movement systems provide additional assistance in maintaining the stability of gaze on visual objects within the surrounds. Automatic compensatory head movements that accompany automatic stabilizing postural movements during upright standing are examples of head movements that assist in gaze stabilization. As described by Nashner L M, Shupert C L, Horak F B. *Head-trunk movement coordination in the standing posture* in Chapter 21 of Pompeiano O, Allum J H J, eds. (1988) Vestibulospinal Control of Posture and Locomotion, Progress in Brain Research, Vol 76. Amsderdam Elsevier Science Publishers, pp. 243-251, which is hereby incorporated by reference, automatic postural responses that sway the body backwards and forwards about the ankles and hips are coordinated with automatic head-neck movements that pitch the head in the opposing direction, thereby helping to maintain the angular orientation of the head relative to the visual surrounds.

During daily life activities, cooperative interactions among the VOR, smooth pursuit, saccadic, optokinetic and vergence eye movement systems, as well as between the postural and head-neck movement systems, allow individuals to maintain their direction of gaze on selected visual objects in their surrounds while performing motor tasks under a wide variety of conditions. For example, when the head is moving and the selected visual target is fixed, the VOR system stabilizes the direction of gaze during more rapid movements while the smooth pursuit system, assisted by the optokinetic system under some conditions, provides gaze stability relative to the slower head movements. When the head is fixed and objects in the visual surround are moving, the smooth pursuit system, again assisted by the optokinetic system under some conditions, stabilizes gaze on objects that are moving slowly. When surrounding objects move more rapidly, the smooth pursuit system cannot maintain gaze stability, and "catch-up" saccadic eye movements are used to re-stabilize the gaze.

When individuals suffer pathological changes in one or more of the five eye movement systems, changes in the adaptive interactions among the five systems may compensate for some of the resulting gaze problems, while other gaze stabilization problems may persist regardless of any adaptive changes. For example, some subjects with defects in the VOR system may attempt to deliberately limit their activities to slower head movements and substitute smooth pursuit movements to stabilize their gaze on fixed objects. When forced to make more rapid head movements, these individuals may use catch-up saccades that, at best, provide only intermittent gaze stability.

Due to wide variations in the relations between pathological and functional mechanisms among subjects, clinicians desiring to improve a subject's gaze control function require information not only of the underlying pathologies but also of the impairments affecting the five control systems and their adaptive interactions. Because systems for maintaining postural and gaze stability share visual, vestibular, and proprioceptive sources of orientation information and the systems for controlling body and head-neck stabilizing movements are coordinated, subjects with pathological changes in systems for maintaining postural stability may also experience problems with gaze stability and visual acuity. Therefore, to effectively plan courses of treatment for individuals with impaired gaze stability, it is frequently necessary to isolate and quantify additional impairment information related to interactions among the systems for postural and head-neck stabilization.

Thus, diagnosing impaired functions within the individual eye movement control systems is difficult unless the conditions of testing are carefully controlled. Accurate diagnoses may only be achieved by precisely controlling the motion conditions to minimize the subject's ability to adaptively substitute alternative control systems. Embodiments of the present invention relate to methods and devices for diagnosing functional impairments among the VOR, smooth pursuit, saccadic, optokinetic and vergence eye movement systems, the postural stability system, and their adaptive interactions. Functional impairments of the gaze stabilization system may be determined by combining or using assessment information derived from an initial test procedure that includes one or more measures of a subject's static visual acuity and/or minimum perception time. The assessment information may then be used to determine one or more measures of a subject's dynamic visual acuity when the head moves in accordance with a protocol and the visual object remains stationary, when the head is stationary and the object moves in accordance with a protocol, or when the head and the object both move in accordance with one or more protocols. Additional embodiments of the invention may combine additional procedures with any of the above procedures, e.g., procedures in which the subject stands freely in the presence of perturbations to postural stability or walks freely.

Further embodiments of the invention pertain to computational methods and devices that differentiate and quantify impairments affecting the gaze stabilization system by combining the derived visual acuity information, and displaying the combined results in graphical or numerical formats. In embodiments that combine the above procedures with additional postural stability procedures, the graphical and numerical results combine visual acuity and postural stability information. Additional embodiments may include methods and devices for displaying visual targets that provide for reliable diagnosing of impairments within individual eye movement control systems. Additional embodiments may include methods and devices for training the individual eye movement control systems.

FIG. 1 is a block diagram illustrating a system which may be used to measure aspects of a subject's gaze stabilization system in accordance with an embodiment of the invention. The system includes a computer 101, which may include a dedicated microprocessor, personal computer, server or other computing device. A display 103 may be in communication with the computer 101, as may be an input device 105 (such as a mouse, keyboard, voice activated input system, light activated input system or touch activated input system). The system may also include a printer 107 or other output device in communication with the computer 101. A motion sensor 109, such as a 3-axis, integrating gyroscope mounted on a headband or other motion sensor, may be used to monitor velocity and direction of head movements of a subject. One example of a system which includes such a headband is the InVision™ system manufactured by NeuroCom International, Inc. of Clackamas, Oreg.

The system may further include a balance testing environment 111, which may include a stationary forceplate, a cushion, or a moveable treadmill in communication with the computer 101. Examples of systems that include forceplates include the BalanceMaster®, the VSR™, the PRO BalanceMaster®, and the SMART BalanceMaster® all manufactured by Neurocom International, Inc. of Clackamas, Oreg. Such a system may include a visual surround or other moveable environment, such as the visual surround included in the EquiTest® or SMART EquiTest® systems manufactured by Neurocom International, Inc. of Clackamas, Oreg.

Figure 2:
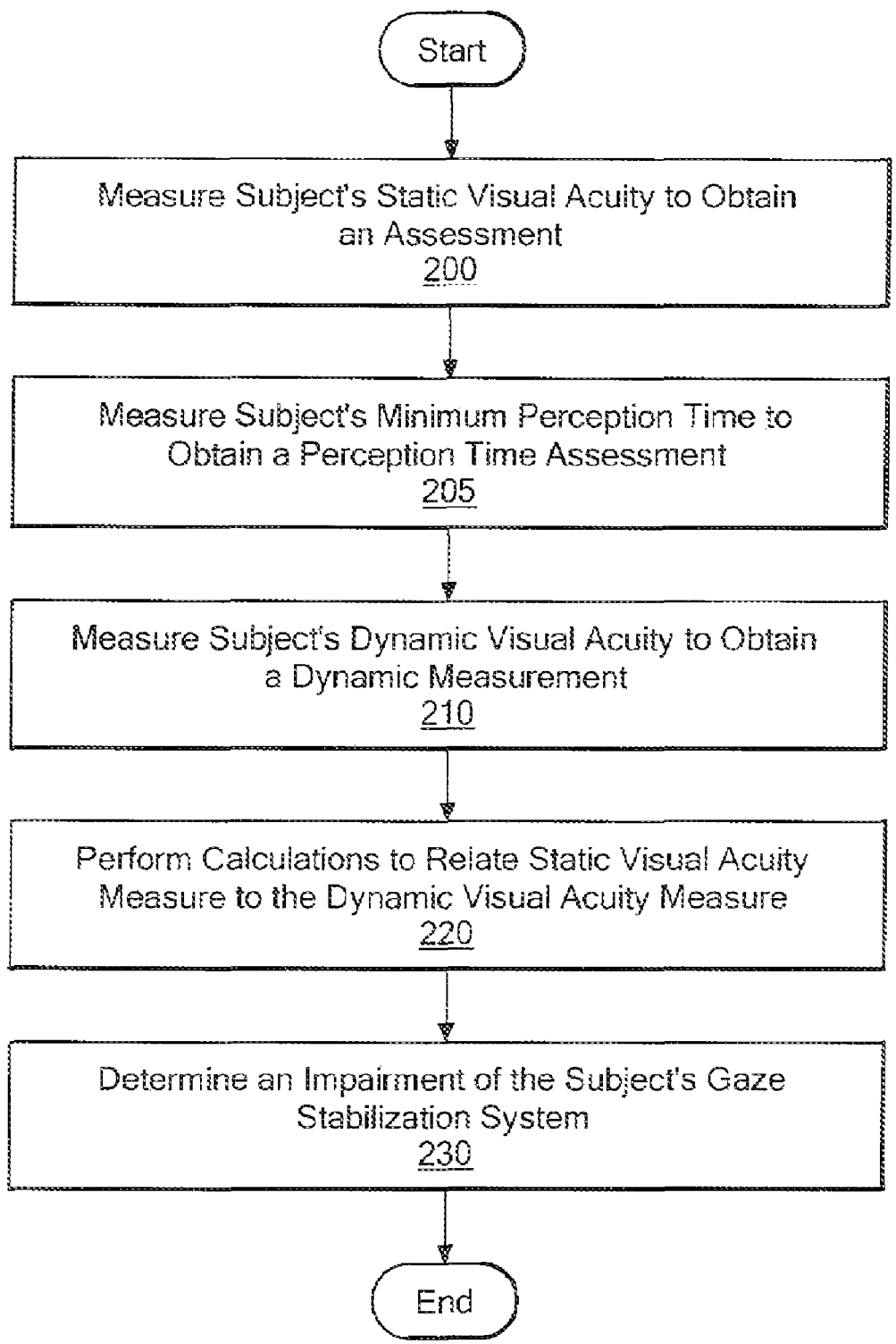
FIG. 2 is a flow chart illustrating a method for diagnosing impairments of a subject's gaze stabilization system according to an embodiment of the present invention.

FIG. 2 is a flow chart illustrating a method for diagnosing impairments of a subject's gaze stabilization system according to an embodiment of the present invention. In step 200, the subject's static visual acuity is measured to obtain an assessment. The subject's static visual acuity may be assessed using any one of a variety of standardized and clinically accepted means, e.g., a Snellen eye chart, Tumpling E chart, or a variety of commercially available mechanized and computerized versions of the eye chart acuity test. Micromedical Technologies of Springfield, Ill., and NeuroCom International, Inc. of Clackamas, Oreg., are two companies that manufacture computerized systems for measuring static visual acuity. In step 205, the subject's minimum perception time is measured to obtain a second assessment. The subject's minimum perception time may be assessed using any one of a variety of commonly used and clinically accepted means. Two examples include, a computerized display system to display a figure on a screen for a pre-determined display time and a film projected figure in which film illumination time is controlled. Test parameters may be set for measurement of the subject's dynamic visual acuity based on the assessment and/or the second assessment as will be described in more detail below.

In step 210, the subject's dynamic visual acuity may be measured to obtain a dynamic measurement. The measurement may be obtained when the subject's head is moving and a display object is fixed, when the subject's head is fixed and the display object is moving, or when the subject's head is moving and the display object is moving. In the case of the head moving, a sensor 109 capable of measuring one or more quantities related to movement may be attached to the subject's head and the resulting head movement quantities transmitted to a computer 101 which may be in communication with a display device 103. The computer may be capable of controlling the time, position, size, shape, orientation, and the large field background of one or more visual display objects. Two examples of displaying an object are a CRT/LCD video monitor and a film/LCD projector projecting onto a reflective screen. Objects displayed by either of these preferred or other display means may include letters or common shapes such as circles, rectangles, triangles, stars, equal and plus signs, etc. Objects may include visual designs and patterns, grids of lines or contrast gratings presented at various orientations. In addition, objects may be displayed with a specified preliminary form and then may change from its preliminary form into a second test form and then back to the preliminary form.

Figure 3:
FIG. 3 shows illustrative preliminary forms and respective test forms of display objects according to an embodiment of the present invention.
Figure 3:
Figure 3:
Figure 3:
Figure 3:
Figure 3:
Figure 3:
Figure 3:

For example, as shown in FIG. 3, the preliminary form of an object may be a circle and the test form of the object may be the letter "C" formed by temporarily eliminating a segment of the circle. By eliminating different segments of the circle to form the letter "C", the display object appears as the letter "C" positioned in different orientations, and the subject may be instructed to report the orientation of the letter "C". Other examples may include a preliminary form in the shape of a circle with the test form having an additional line drawn through the circle to form a capital "Q" at different orientations, a preliminary form in the shape of an oval with the test form having a portion of the oval removed to form the letter "U" at different orientations, or a preliminary form in the shape of an asterisk figure with the test form having some of the intersecting lines removed from the asterisk to form an "X" in different orientations. A "tumbling E" is an example of another object that may be used.

As understood by one skilled in the art, many other combinations of preliminary and test forms may be employed that allow the subject to perceive changes in the form of an object without disrupting the smoothness of the eye movement. The preliminary form and test form of the display object may move periodically along a horizontal, vertical, and/or inclined line. The display object may be presented during a plurality of trials and during each trial the subject may be asked to correctly identify the specified characteristic of the test form of the object. One or more test forms of the display object may be presented at one or more selected times during each trial. The display object may be presented moving in one or more directions. For example, the display object may be moving in one direction during one presentation, with the remaining presentations made with the display object moving in the opposite direction. The ability of the subject to perceive the specified characteristic of the test form of the display object while moving in one direction may then be compared to the ability to perceive the characteristic while the display object moves in the opposite direction.

Referring again to step 210, in one protocol, the subject may be instructed to move the head in a prescribed manner while the computer monitors the head movement and identifies one or more intervals during which the head is moving with a movement criteria. The movement criteria may be a minimum angular velocity of head velocity in a prescribed plane of motion. The computer may then select a display interval during which to display the display object in its preliminary form and/or its test form. The subject may then be asked to identify one or more attributes of the display object. This protocol may be repeated a number of times and the numbers of correct and incorrect identifications may be recorded, e.g., by the computer. A change in the task may be triggered by the relative number of correct and incorrect identifications. For example, the protocol may be repeated with the test made more difficult when the subject makes a predetermined correct number of identifications, e.g., minimum of three correct identifications out of five consecutive trials. Similarly, the test may be terminated when the subject makes a predetermined incorrect number of identifications, e.g., the number of correct identifications is less than three out of five trials. A change in the task may include making one or more changes to the test parameters such as changes to the properties of the display object, the display criteria, or both. For example, the test parameters may be varied to make the test more difficult, e.g., by decreasing the display object size, increasing the display object complexity, reducing or increasing the display object contrast, increasing the movement criteria velocity, changing the movement criteria axis and/or direction, changing the attributes of the large field background, and/or decreasing the maximum display interval. Similarly, the test parameters may be varied to make the test easier.

In the case of the display object moving, the dynamic measurement may be obtained in a way similar to that described above. For example, a sensor capable of measuring angular velocity of movement may be attached to the subject's head and the resulting measures of angular head velocity may be transmitted to a computer. The computer may be in communication with a display device and capable of controlling the time, position, size, shape, and orientation of visual display objects displayed to the subject.

In one protocol, for example, the subject may be instructed to maintain the head in a fixed position while the computer displays an initial fixed position target. The computer identifies display intervals during which the subject's head is within the specified fixed position, with no more than a specified amount or error. For example, the fixed position criteria may be that the subject positions the head to face directly forward with less than a specified number of degrees of position error and/or a specified number of degrees per second in the rate of change of position error. Alternatively, the subject may be required to direct the head to face in any one of a number of positions, each with specified maximum amounts of position error and/or rates of change in position error.

When the subject's head is within the specified fixed position criteria, the computer may then select a display interval during which to present the display object. For example, the display object may be initially stationary and displayed in a holding position and then moved to another prescribed position with a prescribed movement direction and movement velocity. The display object may then disappear. In some embodiments, the holding position may be the center of the display area (which may include a screen) and the direction of the display object motion may be to the left, right, up, down, or along a diagonal. Alternatively, the display object may be moving, rather than initially stationary and then moved to another prescribed position, when the subject is initially asked to follow or watch the display object. The display object may be moving in a continuous movement or with discrete or discontinuous movements. The subject may then be asked to identify one or more attributes of the display object, such as the shape or orientation of the test form.

Processes similar to that described above may then be performed. For example, the protocol may be repeated a number of times and the numbers of correct and incorrect identifications may be recorded by the computer. A change in the task may be triggered by the relative number of correct and incorrect identifications and may include making one or more changes to the test parameters. For example, the test parameters may be varied to make the test more difficult, e.g., by decreasing the display object size, increasing the display object complexity, reducing or increasing the display object contrast, increasing the display object movement velocity, increasing the distance between the holding position and the display object position, changing the direction orientation between the holding position and the display position, changing the display object movement axis and/or direction, changing the attributes of the large field background, moving the large field background either with or independently of the discrete display object, and/or decreasing the maximum display interval. Similarly, the test parameters may be varied to make the test easier.

In the case of the head moving and the display object moving, the dynamic measurement may be obtained in a way similar to that described above by combining aspects of both the head moving and the display object moving processes.

Calculations may be performed to relate the results of the static visual acuity measure to the dynamic visual acuity measure in step 220. A relation between one dynamic measurement (e.g., the visual acuity measured when the subject's head is moving and the display object is fixed) and the subject's static visual acuity may be determined by fixing the size of the display object in relation to the subject's static visual acuity, fixing the duration of time the display object is displayed to allow sufficient time for the subject to perceive the object but insufficient time to perform a catch-up saccadic movement to the object (in normal subject's generally greater than 40 milliseconds and less than 100 milliseconds and, in accordance with one embodiment, the greater of 75 milliseconds or the subject's minimum perception time plus 35 milliseconds), and then determining the maximum head movement velocity during which the subject can correctly identify the object, e.g., during a minimum three of five consecutive trials. For example, the display object size may be twice the size of the smallest object correctly identified during the static visual acuity test. Additional maximum head moving/object fixed stabilization scores may be calculated for various dimensions and directions of head movement (e.g., right to left, left to right, up to down, and/or down to up). The head movement velocity may be fixed and the size of the display object may be reduced until the subject fails to correctly identify the display object, e.g., during a minimum three of five consecutive trials.

A relation between another dynamic measurement (e.g., the subject's visual acuity when the subject's head is fixed and the display object is continuously moving) and the subject's static visual acuity may be determined by fixing the size of the display object in relation to the subject's static visual acuity, fixing the duration of time the display object is displayed to allow sufficient time for the subject to perceive the object but insufficient time to perform a catch-up saccadic movement to the object (generally greater than 40 milliseconds and less than 100 milliseconds and, in accordance with one embodiment, the greater of 75 milliseconds or the subject's minimum perception time plus 35 milliseconds), and then determining the maximum object movement velocity during which the subject can correctly identify the display object, e.g., during a minimum three of five consecutive trials. For example, the display object size may be twice the size of the smallest object correctly identified during the static visual acuity test. Additional maximum head fixed/display object continuously moving stabilization scores may be calculated for various dimensions, and directions of object movement (e.g., right to left, left to right, up to down, and/or down to up). Further, display object movement velocity may be fixed and the size of the display object may be progressively reduced until the subject fails to correctly identify the object, e.g., during a minimum three of five consecutive trials.

A relation between another dynamic measurement (e.g., the subject's visual acuity when the subject's head is fixed and the display object is continuously moving with a patterned large field background that is itself either fixed or is also moving in relation to the display object movement) and the subject's visual acuity may be determined by fixing the size of the display object in relation to the subject's static visual acuity, specifying the pattern and movement characteristics of the large field background, fixing the duration of time the display object is displayed to allow sufficient time for the subject to perceive the object but insufficient time to perform a catch-up saccadic movement to the object (generally greater than 40 milliseconds and less than 100 milliseconds and, in accordance with one embodiment, the greater of 75 milliseconds or the subject's minimum perception time plus 35 milliseconds), and then determining the maximum object movement velocity during which the subject can correctly identify the display object, e.g., during a minimum three of five consecutive trials. For example, the display object size may be twice the size of the smallest object correctly identified during the static visual acuity test and the large field background is a series of black stripes on a white background that move in synchrony with to the display object. Additional maximum head fixed/display object continuously moving stabilization scores may be calculated for various dimensions, and directions of object movement (e.g., right to left, left to right, up to down, and/or down to up) and for various large field background movements (e.g., a fixed background pattern, a background pattern moving in a different direction than the display object, and a patterned background moving in direct opposition to the display object). Further, display object movement velocity may be fixed and the size of the display object may be progressively reduced until the subject fails to correctly identify the object, e.g., during a minimum three of five consecutive trials.

A relation between another dynamic measurement (e.g., the subject's visual acuity when the subject's head is fixed and the display object is discontinuously moving) and the subject's static visual acuity may be determined by fixing the size of the display object in relation to the subject's static visual acuity, instructing the subject to direct gaze towards a focus point (such as a center marker), causing the display object to abruptly appear after a random delay at a predetermined location relative to the center marker, presenting the display object for a predetermined period of time, instructing the subject to identify the object, and then determining a minimum time by reducing the display object presentation time until the subject fails to correctly identify the object, e.g., during a minimum three of five consecutive trials. For example, the display object size may be twice the size of the smallest object correctly identified during the static visual acuity test. Additional minimum times may be calculated for display objects placed in various directions from the central marker (e.g., to the right, left, above, and below).

A relation between another dynamic measurement (e.g., the subject's visual acuity when the subject's head is moving and the display object is moving, either continuously, discontinuously or continuously with a patterned large field background) and the subject's static visual acuity may be determined in a manner similar to that described above with respect to the relations between other dynamic measurements and the subject's static visual acuity.

In step 230, an impairment of the subject's gaze stabilization system may be determined using the static assessment and the dynamic measurements, e.g., using two or more of the five dynamic measurements mentioned above. The relative extent to which impairments in the VOR, smooth pursuit, saccadic, optokinetic and vergence systems each reduce a subject's ability to accurately perceive display objects when the subject and/or the display object is in motion may be determined by comparing results of among any or all five dynamic acuity measures, including head moving/object fixed, head fixed/object continuously moving, head fixed/object discontinuously moving, head fixed/object continuously moving with a patterned large field background, and head moving/object moving (continuously, discontinuously or continuously with a patterned large field background). For example, one method for comparing an individual dynamic measure with a static acuity measure may be to calculate, for that dynamic condition, the ratio between the dynamic and static acuity measures. A second method may be to calculate the acuity differences between the dynamic measure and the static measure. A third method may be to calculate differences or ratios among two or more of the dynamic acuity measures.

In the smooth pursuit eye movement system and the optokinetic eye movement system, subjects with impairments to one or both of these systems may sometimes compensate in part using a combination of head movements and eye movements that are coordinated with one another using the VOR eye movement system. The extent of VOR compensation during assessment of smooth pursuit and optokinetic impairments may be quantified by comparing the display object movement velocity and the component of the head movement velocity in the same direction.

Figure 4A:
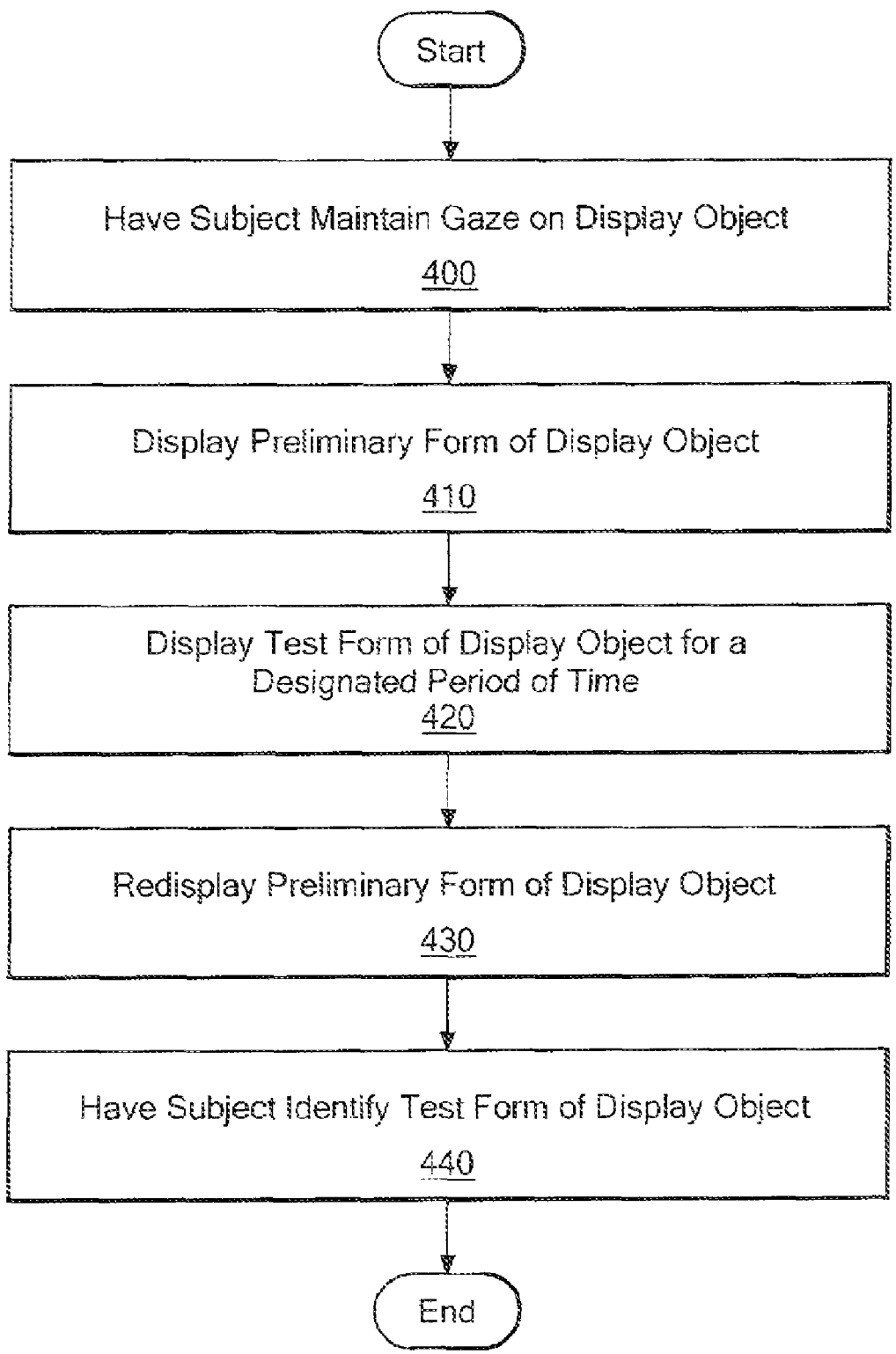
FIG. 4A is a flow chart illustrating a method for testing a subject's smooth pursuit system according to an embodiment of the present invention.

FIG. 4A is a flow chart illustrating a method for testing a subject's smooth pursuit system according to an embodiment of the present invention. To effectively isolate impairments related to the subject's smooth pursuit system and to eliminate the influence of acquisition and catch-up saccadic eye movements, the subject should be smoothly tracking the continuously moving object prior to the presentation of a visual acuity task, while the duration of the acuity task must be sufficiently brief to eliminate the possibility of the subject making a "catch-up" saccadic eye movement. In step 400, a subject may be instructed to maintain gaze on the display object. In step 410, a preliminary form of the display object is displayed. The display object may be displayed in a continuous movement as it moves along a trajectory. At a point in time that cannot be anticipated by the subject and during which the display object is moving at a specified velocity, the display object may change from its preliminary form into one or more test forms. The test form of the display object may be displayed for a designated period of time sufficiently long to enable its recognition but not long enough to allow a catch-up saccade (step 420) before reverting to its original preliminary form (step 430). The subject may then be asked to correctly identify a specified characteristic of the test form(s) of the display object (step 440). The process may be repeated and modified based on the number of correct and incorrect identifications using progressively higher or lower specified velocities until the subject fails to correctly identify the specified characteristic of the test form(s).

Figure 4B:
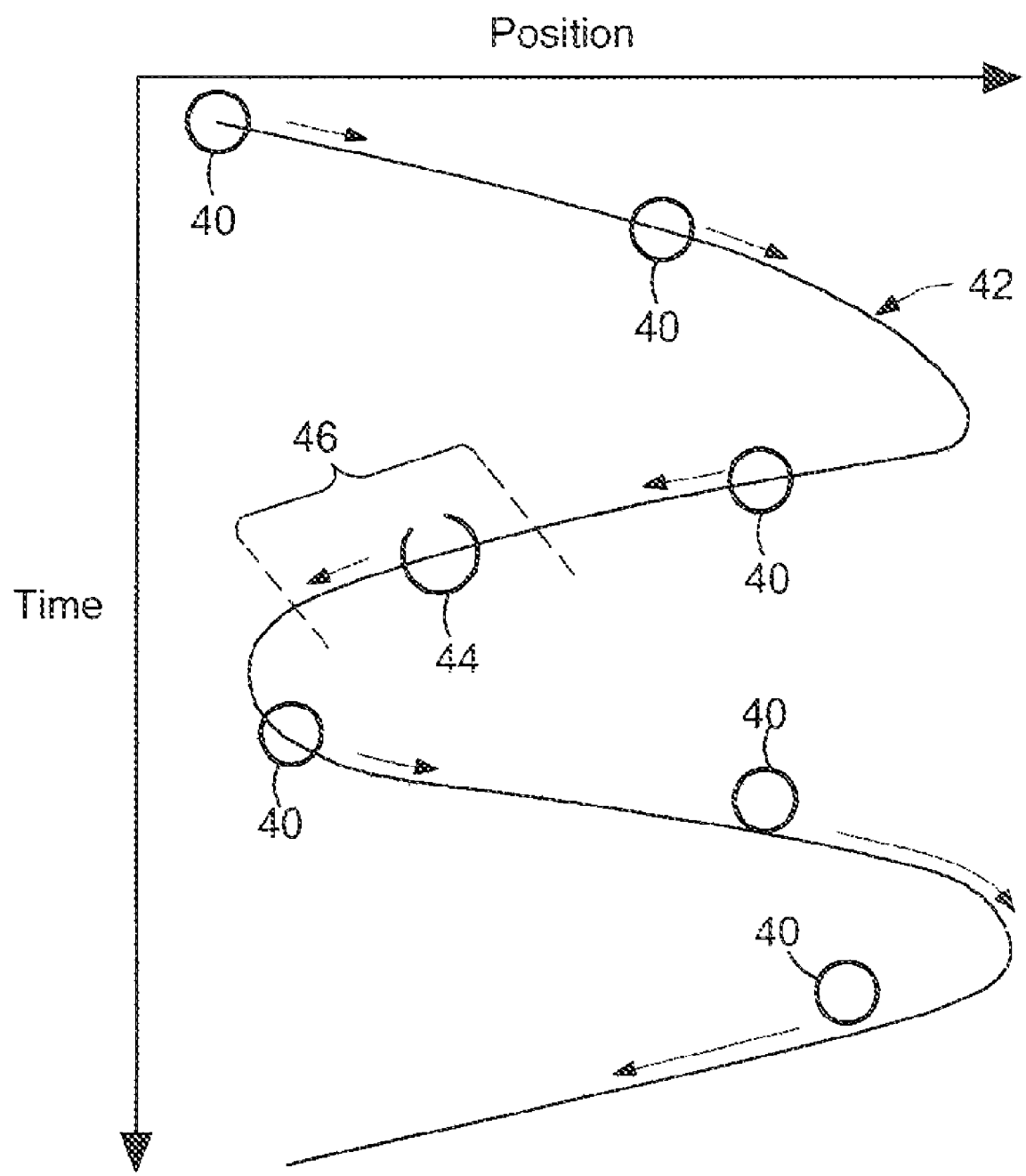
FIG. 4B shows an illustrative smooth pursuit test according to an embodiment of the present invention.

FIG. 4B shows an illustrative smooth pursuit test according to the method described in FIG. 4A. A display object with a specified preliminary form 40 may be displayed in a continuous movement as it moves along a trajectory 42. At a designated point in time, the display object may change from its preliminary form 40 into its test form 44. The display object may remain in the test form 44 for a designated period of time (display interval shown as 46) sufficiently long to enable its recognition but not long enough to allow a catch-up saccade before reverting to its original preliminary form 40. The subject may then be asked to correctly identify a specified characteristic of the test form 44 of the display object.

Figure 5A:
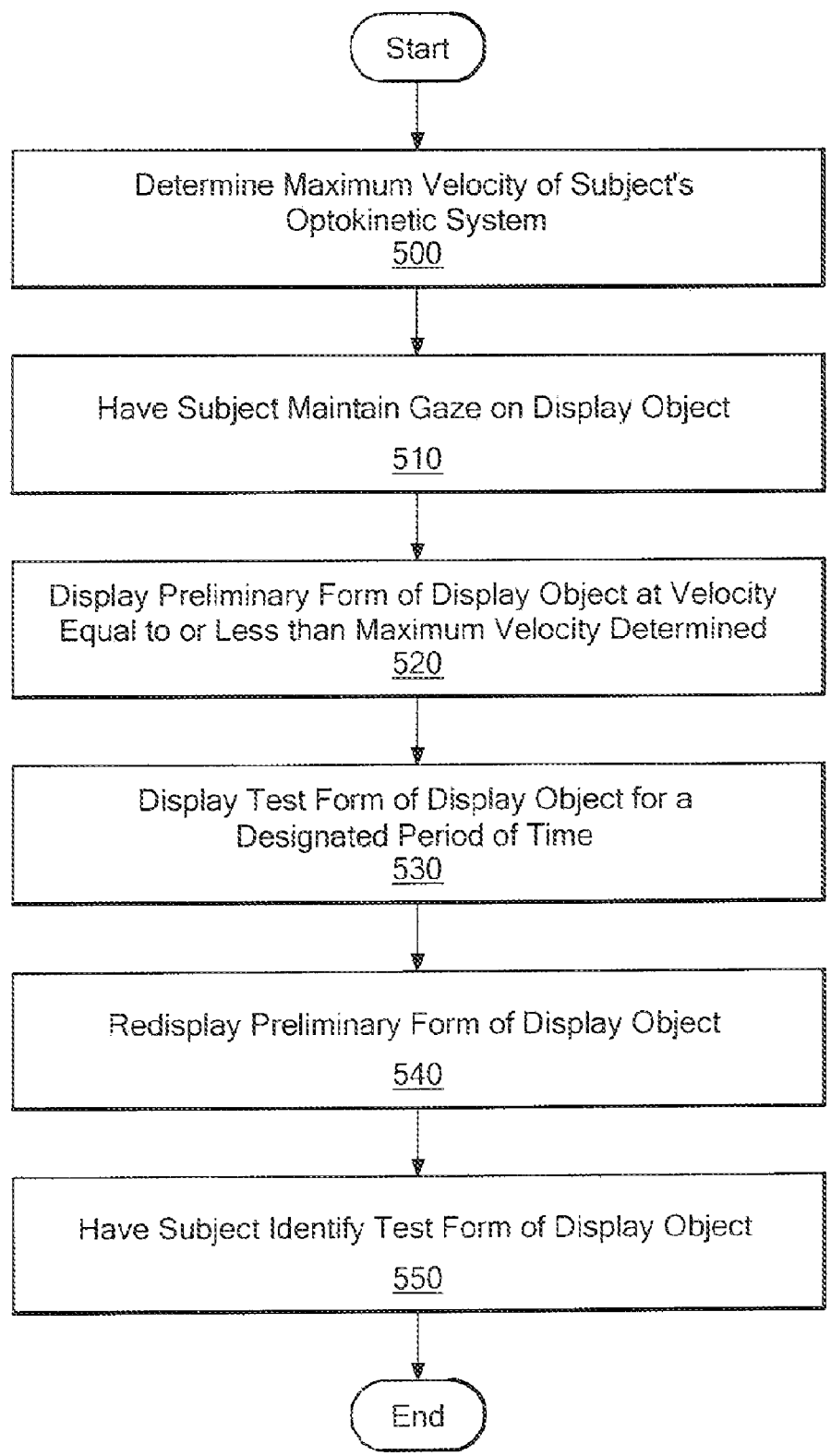
FIG. 5A is a flow chart illustrating a method for testing a subject's optokinetic system according to an embodiment of the present invention.

FIG. 5A is a flow chart illustrating a method for testing a subject's optokinetic system according to an embodiment of the present invention. In this example, the subject's head is fixed and a display object imbedded within a patterned large field background is continuously moved. To effectively isolate impairments related to the subject's optokinetic eye movement system and to eliminate the influence of the smooth pursuit system, the continuous movement of the patterned large field background should be at velocities higher than the maximum velocity capabilities of the subject's smooth pursuit eye movement system. In step 500, the maximum velocity at which the subject can accurately perceive a visual object using the smooth pursuit system may be determined or quantified. In step 510, the subject may be instructed to maintain gaze on a display object imbedded within the patterned large field display as it moves along a trajectory. In step 520, the preliminary form of the display object in the patterned large field display is displayed moving continuously at a velocity equal to or greater than the maximum velocity of the subject's smooth pursuit system determined in step 500. At a point in time that cannot be anticipated by the subject, the display object may change from its preliminary form into one or more test forms. The test form of the display object may be displayed for a designated period of time sufficiently long to enable its recognition but not long enough to allow a catch-up saccade (step 530) before reverting to its original preliminary form (step 540). The subject may then be asked to correctly identify a specified characteristic of the test form(s) of the display object (step 550). The process may then be repeated with successively higher or lower display velocities until the subject fails to correctly identify the specified characteristic of the test form(s) of the display object. The extent to which imbedding the test form of the display object within a patterned large field results in a second maximum velocity at which a subject can maintain visual acuity that is greater than the maximum velocity of the subject's smooth pursuit system provides a functional measure of the optokinetic eye movement system.

Figure 5B:
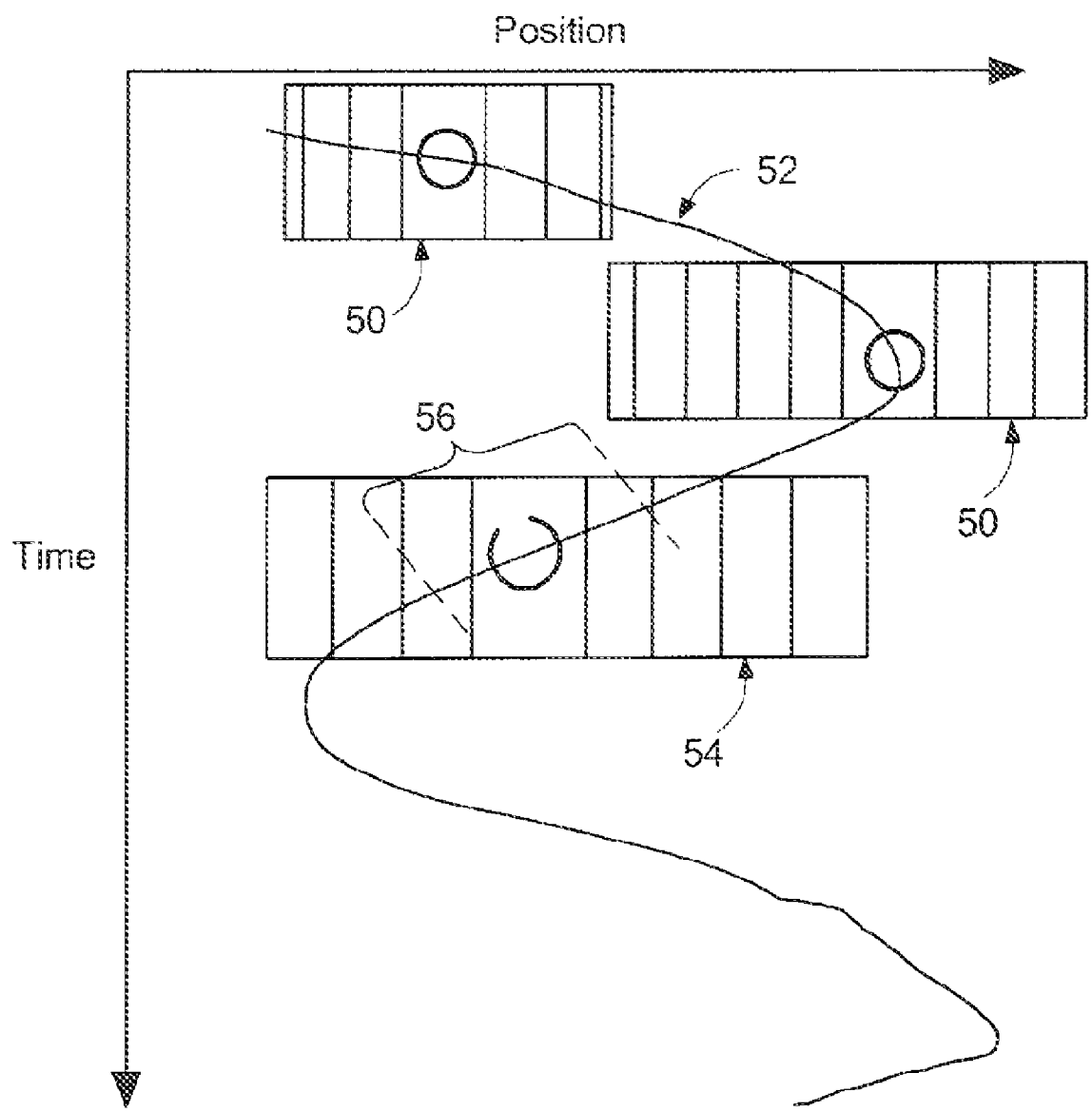
FIG. 5B shows an illustrative optokinetic test according to an embodiment of the present invention.

FIG. 5B shows an illustrative optokinetic test according to the method described in FIG. 5A. After the maximum velocity of the subject's smooth pursuit system is determined, a display object with a specified preliminary form 50 shown in a patterned large field background may be continuously moved along a trajectory 52 at a velocity equal to or greater than the maximum velocity of the subject's smooth pursuit system. At a designated point in time, the display object may change from its preliminary form 50 into its test form 54. The display object may remain in the test form 54 for a designated period of time (display interval shown as 56) sufficiently long to enable its recognition but not long enough to allow a catch-up saccade before reverting to its original preliminary form 50. The subject may then be asked to correctly identify a specified characteristic of the test form 54 of the display object.

Figure 6:
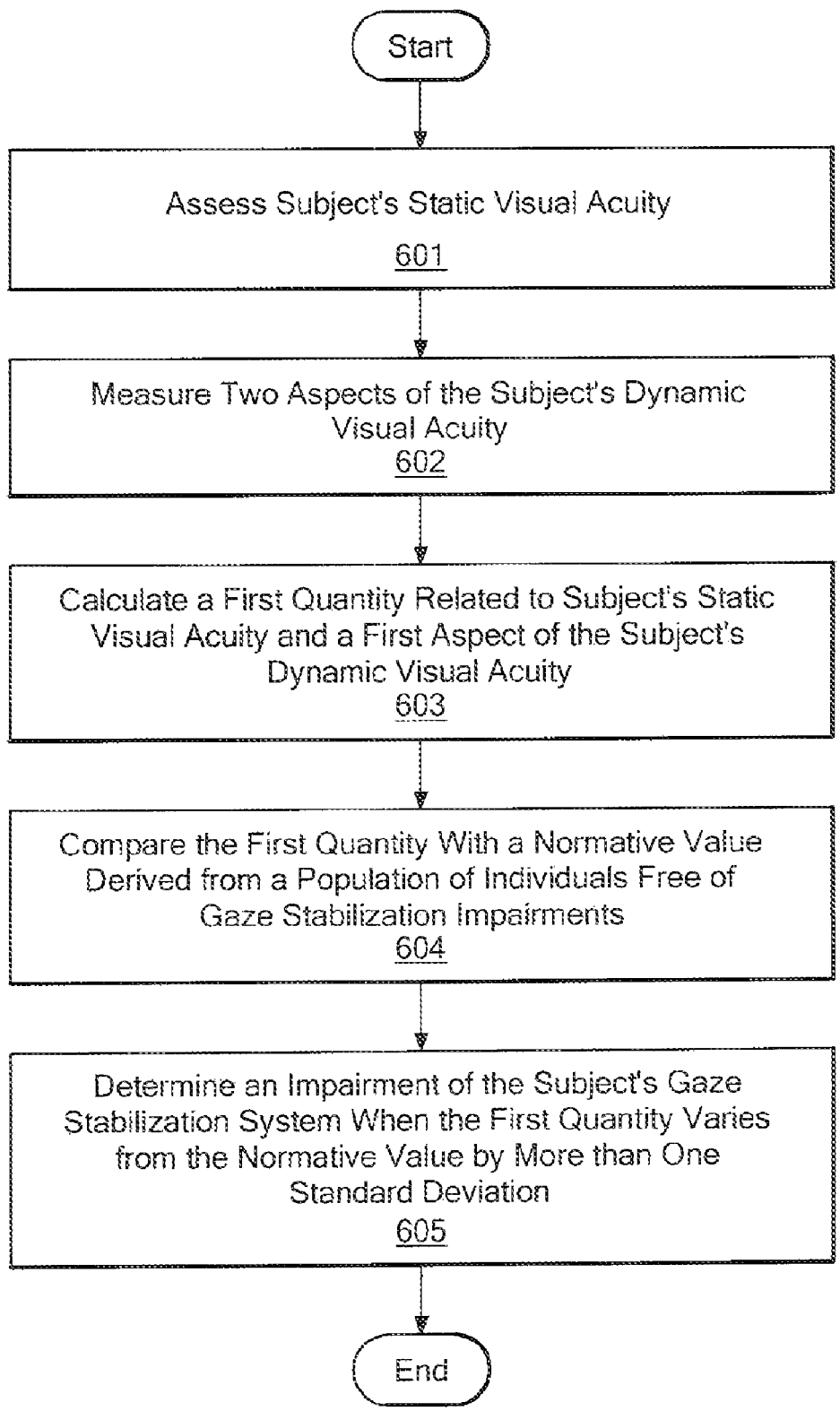
FIG. 6 is a flow chart illustrating a method for diagnosing impairments of a subject's gaze stabilization system employing a test population free of medical problems according to an embodiment of the present invention.

FIG. 6 is a flow chart illustrating a method for diagnosing impairments of a subject's gaze stabilization system employing a test population free of medical problems according to an embodiment of the present invention. In step 601, the subject's static visual acuity may be assessed as described with respect to FIG. 2. At least two aspects of the subject's dynamic visual acuity may then be measured in step 602 (e.g., measuring the subject's visual acuity when his or her head is moving and a display object is fixed, measuring the subject's visual acuity when his or her head is fixed and a display object is moving, measuring the subject's visual acuity when the subject's head is fixed and a display object is discontinuously moving, and/or measuring the subject's visual acuity when the subject's head is fixed and a display object and/or patterned large field background is moving continuously or discontinuously). A first quantity related to both the subject's static visual acuity and a first aspect of the subject's dynamic visual acuity may be calculated (step 603) and the first quantity may be compared (step 604) with a normative value similarly derived from a population of subjects free of gaze stabilization impairments. In step 605, an impairment of the subject's gaze stabilization system may be determined when the first quantity varies from the normative value by more than one standard deviation.

For example, results of the head moving/object fixed, head fixed/object continuously moving, head fixed/object discontinuously moving, head fixed/object and patterned large field background moving continuously and/or head moving/object moving processes described above may be obtained by testing a population of individuals determined to be free of medical problems impacting the functioning of systems controlling their gaze stabilization. Statistical methods described in the prior art may be used to establish normal ranges of results for subjects grouped by age. Statistical quantities for establishing normal ranges may include age-matched population averages, medians, standard deviations, and/or standard errors. Impairments may then be differentiated and quantified in individuals suspected of having problems with gaze stabilization. This may be accomplished by obtaining the head moving/object fixed, head fixed/object continuously moving, head fixed/object discontinuously moving, head fixed/object and patterned large field background continuously moving and/or head moving/object moving results of the subject with suspected problems, and comparing the suspect subject's results with those of the appropriate age-matched normal range. One or more statistical quantities may then be used to determine the extent and characteristics of impairments of subject's gaze stabilization. Such statistical comparisons may include a measurement quantity being considered abnormal that differs by more than one standard deviation from the age-matched normal range average value obtained for that quantity.

Similarly, results of the head moving/object fixed, head fixed/object continuously moving, head fixed/object discontinuously moving, head fixed/object and patterned large field background moving and/or head moving/object moving processes described above may be obtained by testing populations of individuals that are known to successfully perform specified work and/or sports related activities in their daily lives, such activities including flying an aircraft, operating a heavy piece of machinery that moves, playing football, basketball, tennis, etc. Minimum performance ranges of results grouped by specified work and/or sports related activities may be established for the described measures using statistical methods known in the prior art. Statistical quantities may include population averages, medians, standard deviations, and/or standard errors. Limitations in gaze stabilization may then be differentiated and quantified in individuals suspected of having gaze stabilization problems that may compromise their ability to perform the similar work and/or sports related activities safely and effectively. This goal may be accomplished by obtaining the head moving/object fixed, head fixed/object continuously moving, head fixed/object discontinuously moving, head fixed/object and patterned large field background continuously moving and/or head moving/object moving results of the subject with suspected performance limitations, and comparing this subject's results with those obtained from the population of individuals that are known to safely and effectively perform the same work and/or sports related activity. One or more statistical quantities may then be used to determine the extent and characteristics of any performance limitations in the subject's gaze stabilization. Such statistical comparisons may include a measurement quantity being considered abnormal when its value differs from the population average value obtained for that quantity by one or more standard deviations.

Further, specified work and/or sports related activities may be analyzed theoretically to determine the maximum velocities and directions of head and visual object movements, and the types and motions of large field backgrounds. The activities may be further analyzed to determine the minimum acceptable visual acuity requirements. These theoretical values may then be used to derive, for each work and/or sports activity, minimum performance standards for each of the head moving/object fixed, head fixed/object moving continuously, head fixed object moving discontinuously, head fixed/object and patterned large field background continuously moving and/or head moving/object moving tests.

Figure 7:
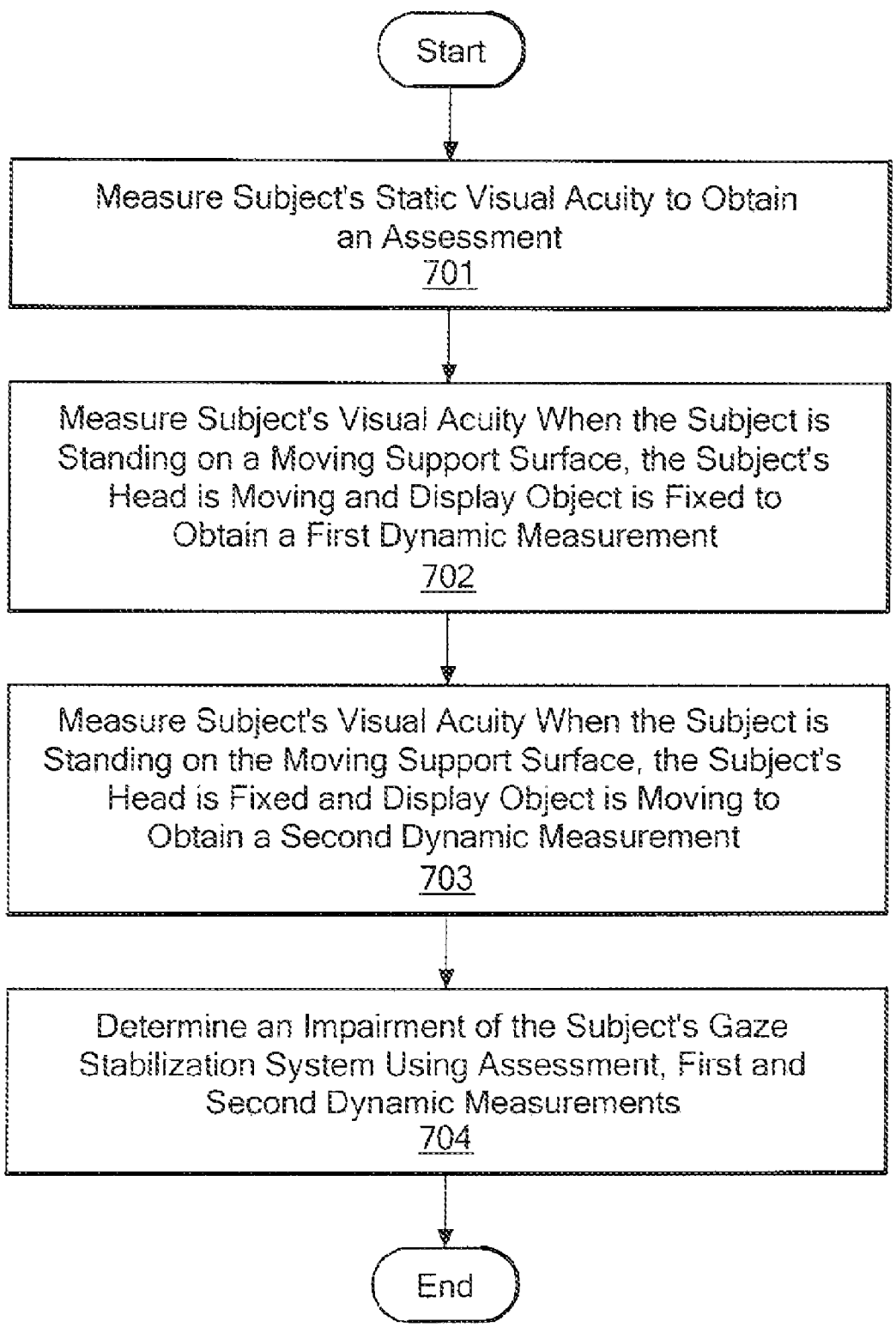
FIG. 7 is a flow chart illustrating a method for diagnosing impairments of a subject's gaze stabilization system employing a free standing balancing task according to an embodiment of the present invention.

Methods and devices described above may be combined with additional methods and devices in which the subject performs one or more visual acuity tests while at the same time performing a specified free standing balance or walking task. For example, FIG. 7 is a flow chart illustrating a method for diagnosing impairments of a subject's gaze stabilization system employing a free standing balancing task according to an embodiment of the present invention. In step 701, the subject's static visual acuity is measured to obtain an assessment as described with respect to FIG. 2. The subject may be directed to perform at least one free standing balance task while measuring the subject's visual acuity in step 702. The free standing balance task may include standing on at least one surface which moves (either with constant velocity or with acceleration), e.g., a treadmill, in relation to the display of the display object. In step 703, the subject's visual acuity is measured when the subject's head is moving and a display object is fixed to obtain a first dynamic measurement. The subject's visual acuity is then measured when the subject's head is fixed and the display object is moving to obtain a second dynamic measurement in step 704.

Other test combinations which may be employed with respect to steps 702-704 may include the following:

1) While performing one or more gaze stabilization tests, the subject may stand on one or more support surfaces and/or may be surrounded by one or more surfaces that are capable of being actively and independently moved about one or more axes. Sensing devices may measure one or more quantities related to the motions of the standing subject, the measurement quantities may be transmitted to a computer and the computer may cause the one or more support and surrounding surfaces to move in functional relation to the subject's motions. In one embodiment, one or more compliant elements may cause the surface to move passively about one or more axes in response to the contact forces exerted by the freely standing subject.

In combining gaze stabilization and freely standing balance tasks, one or more surfaces may be caused to commence continuous movement in temporal relation to presentation of the display object and the large field background. Initiating surface motions well in advance of the display object presentation may provide sufficient time to coordinate postural and gaze stabilizing movements. Beginning surface motions, display object presentations, and large field background motions in close temporal relation, in contrast, may provide little, if any, time for coordination of postural and gaze movements.

2) While performing one or more gaze stabilization tests, the subject may stand on a support surface that is capable of being actively moved about one or more axes. In one embodiment, the support surface may move abruptly in temporal relation to the presentation of the display object and the large field background. Again, initiating surface motions well in advance of the display object presentation with or without large field background motions may provide sufficient time to coordinate postural and gaze stabilizing movements. Beginning the surface motions and display object presentations, with or without large field background motions, in close temporal relation, in contrast, may provide the subject with little time for coordination of postural and gaze movements.

3) While performing one or more gaze stabilization tests, the subject may walk on a treadmill. The treadmill belt may move continuously at a constant velocity or may be under active control of a computer. In accordance with one embodiment, the velocity of treadmill belt movement may change abruptly in temporal relation to the presentation time of the display object. The display object may or may not also include a moving large field background. Abrupt changes may include causing a fixed belt to begin moving, or causing the velocity of the moving belt either to change abruptly or to cease moving. Changes in treadmill belt motions initiated well in advance of the display object presentation may provide the subject with sufficient time to coordinate gait and gaze stabilizing movements. Initiating changes in treadmill belt motion and display object presentations in close temporal relation, in contrast, may provide the subject with little time for coordination of gait and gaze movements.

In step 705, the assessment and the first and second dynamic measurements may then be used to determine an impairment of the subject's gaze stabilization system in accordance with one or more of the methodologies described above.

Figure 8:
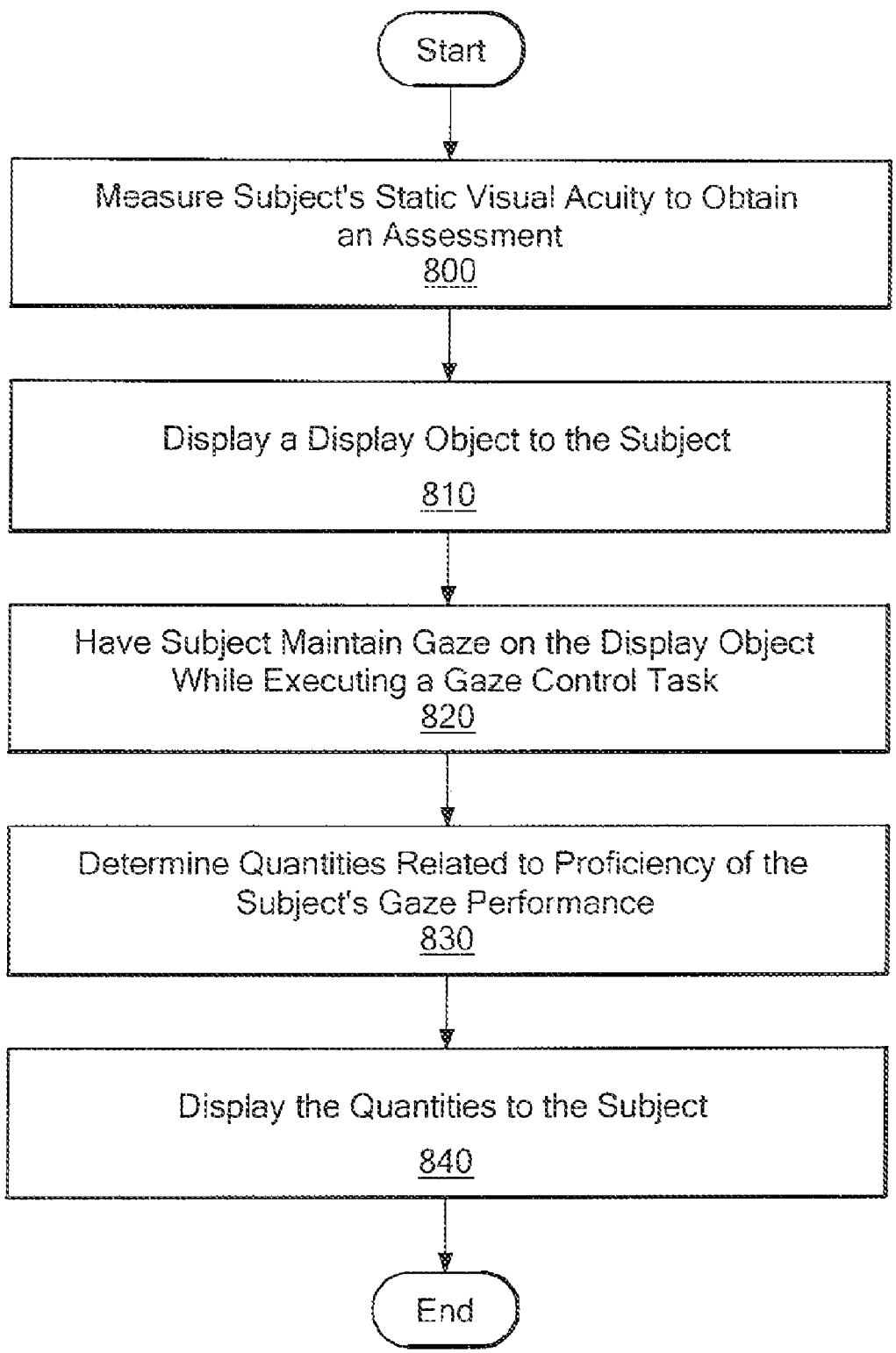
FIG. 8 is a flow chart illustrating a method for training a subject's gaze stabilization system according to an embodiment of the present invention.

FIG. 8 is a flow chart illustrating a method for training a subject's gaze stabilization system according to an embodiment of the present invention. Multi-component systems such as that controlling gaze may be trained to achieve higher levels of performance in two ways. (1) Training may improve the performance capabilities of individual movement systems. Applications of this principle to the gaze control system may include training exercises directed to: (a) the smooth pursuit system to improve an individual's ability to track faster moving visual targets, (b) the saccadic system to improve the speed and accuracy of movements to acquire new targets, (c) the VOR system to improve the stability of gaze during more rapid head movements, (d) the optokinetic system to improve an individual's ability to track targets imbedded within large moving visual fields, and (e) the vergence system to improve an individual's ability to accurately perceive objects when distances between the individual and the object are changing. An example of this type of learning is training an individual to increase the input-output gain of the VOR. (2) When one movement control system is impaired, an individual can be trained to substitute a healthy movement control system to accomplish a task typically performed using another impaired system.

New skills are acquired most efficiently when they are practiced in the following sequence: (a) in isolation with immediate and continuous feedback of performance, (b) in isolation with performance results delayed until the task is completed, and (c) incorporated as part of larger tasks related to those experienced in daily life activities. This sequence of training pertains to training exercises directed to both improving performance of individual gaze control systems and substituting one gaze control system for another impaired system. Translated to the acquisition gaze stabilization skills, this principle indicates that gaze training should include the following: (a) exercises focused on individual gaze control systems both with immediate and delayed feedback of performance, and (b) exercises that, depending on the needs of the individual subject, incorporate the trained gaze control systems into daily life, sports, and occupational tasks which require effective use of the trained gaze control system.

Skills are learned most effectively when their difficulty levels are adjusted on a regular basis so that subjects are able to successfully complete tasks approximately one-half the time. Translating this principle to training gaze stabilization skills indicates that function of the gaze control systems being trained along with subject performance of training tasks should be assessed on a regular basis and the difficulty levels of tasks adjusted accordingly.

In step 800, the subject's static visual acuity is measured to obtain an assessment as described with respect to FIG. 2. In step 810, the display object may be displayed to the subject as described above. A visual parameter of the display object may be set in accordance with the static acuity assessment such that at least one visual property of the display object may be correctly identified when the subject's gaze is centered on the display object to within a prescribed level of accuracy.

In step 820, a subject maintains gaze on the display object while executing a gaze control task. The subject and/or the display object may be moving according to one or more protocols, such as described above. For example, the subject may be instructed to voluntarily move one or more parts of the body including the following protocols: (1) while seated or standing moving the head left and right as if saying "no," moving the head up and down as if saying "yes," tilting the head to the left and right, and any combination thereof; (2) while seated leaning forward and backward or to the left and right; and (3) while standing stepping forward and backward or to the left and right. Methods may include the use of external means in contact with the subject's body to move one or more body parts including placing the subject in a position of equilibrium on a support surface and then moving the support surface according to a protocol. Methods may include having the subject move one or more body parts according to a protocol while the subject is placed in a position of equilibrium on a support surface that is moving according to a second protocol. Methods may also include placing the subject in a position of equilibrium on a support surface, measuring a quantity related to the subject's equilibrium, and moving the support surface in functional relation to the measured equilibrium quantity. When the display object is moving, it may be continuously moving, may be discontinuously moving, or may be continuously moving in a patterned large field background.

The display object may be displayed in its preliminary form and its test form. The test form of the display object may be displayed during one or more prescribed points in time during the execution of the task. The size of the display object and/or the test form may be set relative to the subject's static acuity assessment such that it may be correctly identified only when the gaze at the time of presentation is centered on the object within a prescribed level of accuracy. The subject may be instructed to identify the test form when it appears.

In step 830, a quantity related to the proficiency of the subject's gaze performance may be determined at one or more selected times during execution of the gaze control task. To determine the quantities on a continuous basis during performance of the task, individual test forms may be displayed on a periodic basis and the subject may be instructed to identify each occurrence of the test form. The subject is maintaining gaze within the prescribed level of accuracy during those portions of the task in which the test forms are correctly identified.

The following methods may be employed to record each attempt by the subject to identify a test form. The subject may identify the test form, the identity is recorded, for example, by a human operator or a device, such as a voice recognition device, and compared to the actual displayed test form. The method may include displaying the test form with a directional property, such as an up, down, left, or right orientation. The subject may indicate the orientation of the test form, for example, by verbally identifying the direction or by using a body movement. Body movements may be recorded, for example, by a human operator or by a force or position sensing device. The indicated orientation may then be compared to the actual orientation of the test form.

A quantity related to the proficiency of the subject's gaze control performance may be used to alter the difficulty of the visual task. Such methods may include increasing the difficulty level of the gaze control task when a quantity related to the proficiency of the subject's gaze control performance exceeds a specified maximum performance level, and decreasing the difficulty level of the gaze control task when the proficiency quantity falls below a minimum specified performance level.

A number of methods may be used to increase or decrease the difficulty of a gaze control task. In embodiments that include moving the display object, methods may include increasing or decreasing the velocity and/or amplitude of target movement, varying target movement velocity and/or amplitude on a periodic or random basis, altering the trajectory of target movement, or combining two or more of these methods. Alterations in movement trajectory may include changing from one movement dimension to another, and changing from movement in a single dimension to movement combining two or more dimensions. Examples of multi-dimensional target movements include elliptical or rectilinear movement trajectories combining up-down, left-right, and forward-backward dimensions. Other examples of multi-dimensional target movement includes moving the target about a rotational axis while simultaneously translating along an elliptical or rectilinear trajectory.

In embodiments that include moving the subject, methods may include altering the trajectory of the subject's movement on a periodic or random basis, altering the velocity and/or amplitude of movement on a periodic or random basis, or any combination thereof. Alterations in the trajectory of the subject's movement may include changing from one movement dimension to another and from movement in a single dimension to movements combining two or more dimensions. Examples of movement dimensions that change the direction of the subject's gaze are multi-dimensional head movements include elliptical or rectilinear movements combining up-down (pitch), left-right (yaw), and left-right tilt (roll) dimensions.

In embodiments in which both the subject and the display object are moving, methods for altering the difficulty of the gaze control task may include measuring a quantity related to movement of the subject, and moving the display object in functional relation to the measured body movement quantity. In one example, the difficulty of a gaze control tasks may be reduced by measuring a quantity related to the rotational movement of a standing or seated subject's head and then moving the display object in direct relation to the measured rotation quantity such that the rotational motion of the display object relative to the subject's head is reduced. In another example, the difficulty of a gaze control tasks may be increased by measuring a quantity related to the rotational movement of a standing or seated subject's head and then causing the display object to move in opposition to the measured rotation quantity such that the rotational motion of the display object relative to the subject's head is increased. An additional example includes placing a subject in a position of equilibrium on a support surface, measuring a quantity related to the stability of the subject, and moving the display object in functional relation to the measured stability quantity.

In step 840, one or more quantities related to the proficiency of the subject's gaze control performance may be displayed to the subject. The quantities may be displayed to the subject either on a continuous basis during performance of the task or as knowledge of results upon completion of the task. One method for continuously displaying a quantity related the subject's gaze performance is to modify an attribute of the display object in relation to the identification. Examples of modifications may include coloration of a portion of the display object, for example, causing a green coloration when the identification is correct and a red coloration when incorrect. Other methods may include auditory cues, e.g., provided by the operator or sound generating devices, and/or tactile or positional stimuli, e.g., generated by a movement or force generating device in contact with the subject.

Although the above discussion discloses various exemplary embodiments of the invention, it should be apparent to those skilled in the art that variations and modifications may achieve some of the advantages of the invention without departing from the true scope of the invention. Accordingly, other embodiments are within the scope of the following claims.

What is claimed is:

1. A method for training a subject's gaze stabilization system, the method comprising:
    measuring the subject's static visual acuity to obtain an assessment;
    displaying a display object to the subject, such that displaying includes displaying a preliminary form of the display object, displaying a test form of the display object, and redisplaying the preliminary form of the display object, the display object having at least one parameter based on the assessment;
    having the subject maintain gaze on the display object when the subject and the display object are moving relative to one another; and
    having the subject identify the test form of the display object.

2. A method according to claim 1, wherein having the subject maintain gaze on the display object occurs when a subject's head is fixed and the display object is continuously moving, when the subject's head is fixed and the display object is discontinuously moving, when the subject's head is fixed and the display object is continuously moving and is displayed in a patterned large field background, when the subject's head is moving and the display object is fixed, when a subject's head is moving and a display object is continuously moving, when a subject's head is moving and a display object is discontinuously moving, when the subject's head is moving and the display object is continuously moving and is displayed in a patterned large field background, or any combination thereof.

3. A method according to claim 1, further comprising:
    moving the display object according to a protocol.

4. A method according to claim 3, further comprising:
    having the subject move according to a second protocol.

5. A method according to claim 1, further comprising:
    having the subject move according to a protocol.

6. A method according to claim 1, wherein the assessment includes a minimum interval for the subject to correctly identify a visual object and displaying the test form includes displaying the test form for a display interval that is greater than or equal to the minimum interval.

7. A method according to claim 1, further comprising:
    determining a first maximum velocity of a visual object that the subject correctly perceives using the subject's smooth pursuit system, wherein displaying a display object includes moving the display object at a velocity equal to or less than the first maximum velocity.

8. A method according to claim 7, wherein displaying a display object further includes moving the display object at a velocity equal to or greater than the first maximum velocity.

9. A method according to claim 7, further comprising:
    determining a second maximum velocity of the visual object that the subject correctly perceives using the subject's optokinetic system.

10. A method according to claim 1, wherein the assessment includes a minimum size of a visual object that the subject correctly identifies and displaying a display object includes displaying the display object at a display size that is greater than or equal to the minimum size.

11. A method according to claim 1, further comprising:
having the subject perform at least one free standing balance task while maintaining gaze on the display object.

12. A method according to claim 11, wherein having the subject perform at least one free standing balance task includes having the subject stand on at least one surface which moves in relation to a display of the display object.

13. A method according to claim 12, wherein the surface is a force plate, a treadmill, or a combination thereof.

14. A method according to claim 11, wherein having the subject perform at least one free standing balance task includes surrounding the subject with a visual surround.

15. A method according to claim 1, further comprising: determining a quantity related to proficiency of the subject's gaze performance at selected times based on the subject identifying the test form.

16. A method according to claim 15 further comprising displaying the one or more quantities to the subject.

17. A method according to claim 16 wherein determining a quantity related to proficiency of the subject's gaze performance includes the subject's gaze performance related to the subject's vestibule-ocular reflex system, the subject's smooth pursuit eye movement system, the subject's optokinetic eye movement system, the subject's saccadic movement system, the subject's vergence eye movement system, or any combination thereof.

18. A method according to claim 11, wherein having the subject perform at least one free standing balance task includes having the subject stand on at least one surface which moves according to a protocol.

19. A method according to claim 1 further comprising:
having the subject move one or more body parts according to a protocol while the subject is placed on a support surface that is moving according to a second protocol.

20. A method according to claim 1, further comprising having the subject identify a specific characteristic that distinguishes the test form from the preliminary form.

21. A method according to claim 3, wherein moving the display object according to a protocol further comprises positioning the display object in different orientations.

22. A method according to claim 21 further comprising having the subject identify the orientation of the test form.

23. A method according to claim 1, wherein the display object is displayed such that an individual eye movement control system is used, wherein the individual eye movement control system is at least one of a vestibule-ocular reflex system, a smooth pursuit eye movement system, a saccadic movement system, an optokinetic movement system, and a vergence eye movement system.

24. A method according to claim 1 wherein having the subject maintain gaze on the display object includes having the subject maintain gaze on the display object during a change in the display object from the preliminary form to the test form and then back to the preliminary form.

* * * * *